United States Patent
Knox et al.

(10) Patent No.: US 10,668,302 B2
(45) Date of Patent: Jun. 2, 2020

(54) USE OF ANCILLARY DEVICES/ACCESSORIES IN RADIOTHERAPY SYSTEMS

(71) Applicant: Elekta AB (Publ), Stockholm (SE)

(72) Inventors: Christopher Charles Knox, West Sussex (GB); Neil Winchester, Tunbridge Wells (GB); David Anthony Roberts, West Sussex (GB); Jill Stief, East Sussex (GB)

(73) Assignee: ELEKTA AB (PUBL), Stockholm (SE)

( * ) Notice: Subject to any disclaimer, the term of this patent is extended or adjusted under 35 U.S.C. 154(b) by 333 days.

(21) Appl. No.: 14/522,336

(22) Filed: Oct. 23, 2014

(65) Prior Publication Data

US 2015/0119625 A1     Apr. 30, 2015

(30) Foreign Application Priority Data

Oct. 24, 2013  (GB) .................................. 1318805.7
Jul. 24, 2014  (GB) .................................. 1413104.9

(51) Int. Cl.
    *A61N 5/10*     (2006.01)
(52) U.S. Cl.
    CPC ......... *A61N 5/1049* (2013.01); *A61N 5/1047* (2013.01); *A61N 5/1064* (2013.01);
    (Continued)
(58) Field of Classification Search
    None
    See application file for complete search history.

(56) References Cited

U.S. PATENT DOCUMENTS

2007/0106152 A1   5/2007   Kantrowitz et al.
2008/0031414 A1*  2/2008   Coppens ................. A61B 6/04
                                                        378/65

(Continued)

FOREIGN PATENT DOCUMENTS

EP     0 314 214 A2     5/1989
GB     2512384          10/2014

(Continued)

OTHER PUBLICATIONS

GB Search Report, issued in corresponding Application No. GB1318805.7, dated May 20, 2014, one (1) page.

*Primary Examiner* — Amelie R Davis
(74) *Attorney, Agent, or Firm* — Finnegan, Henderson, Farabow, Garrett & Dunner, L.L.P.

(57) ABSTRACT

A system or use with a radiotherapy system includes a scanner for producing images of at least one object within an imaging volume, a radiotherapy apparatus including a source of therapeutic radiation adapted to deliver a beam of radiation into the at least one object, a treatment planning system for controlling the source so as to deliver radiation in accordance with a predetermined plan for treating a patient and with the images of the at least one object, and at least one device within and/or adjacent to the imaging volume. The at least one device comprises at least one first marker which is visible to the scanner and at least one MR second marker which is visible to an MR scanner. The system further comprises a database containing data including the markers associated with the at least one device and at least its geometric and density characteristics.

16 Claims, 3 Drawing Sheets

(52) U.S. Cl.
CPC ......... *A61N 5/1065* (2013.01); *A61N 5/1067* (2013.01); *A61N 2005/1051* (2013.01); *A61N 2005/1055* (2013.01)

(56) References Cited

U.S. PATENT DOCUMENTS

| | | | |
|---|---|---|---|
| 2009/0013468 A1 | 1/2009 | Bourne et al. | |
| 2009/0105583 A1* | 4/2009 | Martin | G01T 1/1603 600/422 |
| 2011/0123083 A1* | 5/2011 | Ojha | G01N 24/08 382/131 |
| 2013/0035585 A1* | 2/2013 | Martens | A61B 5/055 600/411 |
| 2013/0329856 A1* | 12/2013 | Kuwahara | A61N 5/1039 378/62 |
| 2015/0224341 A1* | 8/2015 | Vahala | G01R 33/4808 600/411 |

FOREIGN PATENT DOCUMENTS

| | | |
|---|---|---|
| WO | WO 97/40766 A1 | 11/1997 |
| WO | WO 2005/016140 A1 | 2/2005 |

\* cited by examiner

USE OF ANCILLARY DEVICES/ACCESSORIES IN RADIOTHERAPY SYSTEMS

CROSS REFERENCE TO RELATED APPLICATION

The present application claims the benefits of priority to GB 1318805.7, filed on Oct. 24, 2013, and GB 1413104.9, filed Jul. 24, 2014. The entire content of each of these applications is incorporated herein by reference.

FIELD OF THE INVENTION

The present invention relates to radiotherapy, particularly but not exclusively Magnetic Resonance (MR) guided radiotherapy.

BACKGROUND ART

Incorporating real-time image guidance into radiotherapy can improve tumour targeting accuracy, enabling better avoidance of critical structures and reducing side effects. Such guidance is of particular benefit if a non-ionizing imaging technique such as MRI (magnetic resonance imaging) is employed. Work is currently being undertaken to integrate a linear accelerator with an MR scanner. By integrating high-quality MRI with a source of therapeutic radiation, such as a linear accelerator, tissue can be tracked online and therapeutic radiation beams can be guided to their targets (which may be moving and deforming, such as when the patient breathes) with sub-millimetre precision during treatment.

Radiotherapy frequently utilises various devices and accessories to position a patient; these can include couches, patient supports and replaceable top surfaces therefor, head frames in all types of radiotherapeutic apparatus and (in the case of an MR-Linear Accelerator (MRL), where the patient is also imaged) RF imaging coils and associated stands, etc. If these accessories are located in the path of the radiotherapeutic beam, they may affect the efficacy with which the beam provides the therapy to the patient. There is often a predetermined treatment plan for a particular patient, with an automated treatment planning system (TPS) controlling the relative positions and/or orientation of the patient, the MR scanner and the linear accelerator, and the radiation produced by the linear accelerator to achieve this plan, based on images obtained from the MR scanner. However, non-biological objects such as the devices/accessories will not usually be clearly visible to an MR scanner, and thus cannot be taken into account in an automated treatment planning process; accordingly an operator has to carefully locate and orientate such devices prior to treatment, and manually input information of their location, orientation and composition into the TPS in order for the radiotherapy to be applied in accordance with the predetermined treatment plan. This is time-consuming, and does not account for any movement which may occur during a radiotherapy treatment.

SUMMARY OF THE INVENTION

The present invention therefore provides a system for use with a radiotherapy system comprising: a scanner for producing images of at least one object within an imaging volume, a source of therapeutic radiation adapted to deliver radiation into the or each object, a Treatment Planning System (TPS) for controlling the source so as to deliver radiation in accordance with a predetermined plan for treating a patient and with images of the or each from the scanner of the imaging volume, and one or more devices/accessories within and/or adjacent the imaging volume, wherein the or each device comprises at least one marker which is/are adapted to be visible to the scanner and at least one MR marker which is/are adapted to be visible to an MR scanner, the or each marker/MR marker being adapted accurately to identify the device and its position in relation to the volume, and wherein the system further comprises a database containing data including the marker(s) associated with the device and at least the geometric and density characteristics of the device. With such an arrangement the TPS can accurately identify the device/accessory and its position from the or each marker/MR marker (an MR marker is a marker which is clearly visible to an MR scanner), acquire its size, shape and density profile (all of which determine the disturbance the device will create in the radiotherapeutic beam) and thus adjust the treatment plan to take account of that disturbance to ensure that the therapy is applied in accordance with the predetermined treatment plan. Such a system and devices for use therewith can be for use with any type of radiotherapeutic apparatus, although preferably the radiotherapy apparatus is a magnetic resonance (MR)-guided radiotherapy system, and the scanner is an MR scanner. Where the scanner is not an MR scanner, for example a CT scanner, the first marker must be visible to the CT or other scanner; it may also be visible to an MR scanner (in which case there may only be one marker). Alternatively there may be one or more markers which are visible to the CT or other scanner, and one or more MR markers. The MR scanner picks up the position and/or type of MR marker during imaging, and/or the spatial relationship between a plurality of markers, and the TPS acquires this information in the course of analysing the image for the known purpose of controlling the source so as to apply the appropriate treatment plan. Because the MR imaging is carried out during treatment, any movement or deformation of the devices can be observed by the MR scanner (because it picks up any movement of the MR marker(s) associated with the device), so that the TPS can make the necessary adjustments to ensure the predetermined treatment plan is adhered to. This enables a much more efficient approach to be made to treatment by MR linac, which conventionally tries to avoid placing any object in the path or vicinity of the radiotherapeutic beam in case the object had an effect on the beam and on the radiation dose received by the patient.

The MR marker may be a unique marker (i.e. it may be uniquely associated with a particular device or accessory), and it may be adapted to be capable of indicating the orientation of the device with respect to the volume—this information being included in the database. There may be a plurality of markers associated with a device; in this case, the markers could be similar, with the number and/or spatial disposition of these being sufficient to provide the TPS with a unique identifier for the particular device, as the TPS has simply to match the MR marker data it acquires from the MR scanner to the data in the database. Additionally or alternatively a device may comprise one MR marker (or a particular combination of different MR markers) adapted to identify that device (i.e. a uniquely configured MR marker) in combination with one or more other MR markers for providing information about the position/orientation of the device relative to the volume to the TPS. Further, the disposition of a plurality of MR markers could also enable the orientation of the device to be monitored, so that the TPS is able to make adjustments if a device shifts orientation but not location. The database may include data for a range of devices, in which case the TPS can, from the images captured by the MR scanner of the MR marker(s) and/or its/their disposition/orientation, identify the device from among the range of different devices in the database and determine the position and orientation of the device relative to the volume within the MR scanner where radiotherapy is to be applied; the TPS then calculates, using the position/orientation of the device and the geometric density profile of the device in the database, the effect on the radiation beam which would be caused by the presence of the device, and adjusts the treatment plan so as to ensure that the radiation is delivered to the patient in accordance with the predetermined treatment plan.

Some devices, such as patient supports and replaceable top surfaces therefor, are provided with visible markings or indicia, used for identification and/or for the purpose of manually positioning the patient in the right location and/or orientation on the support. The marker(s) and/or MR marker(s) may be located on or in the device relative to these indicia, and these positional relationships may be included in the data stored in the TPS. This is advantageous when the device is a patient support or a replaceable cover or top surface for a patient surface, and is in use with an MRL; the imaging volume within the MR scanner is often smaller than the overall volume (usually towards the centre of the cylindrical space within which the patient is positioned), and therefore markers positioned near to the edge of the device may not be within, or close enough to, the imaging volume to be detected by the MR scanner. Accordingly the MR markers may be located centrally, so as to be detectable in use by the MR scanner, whilst the visible markings would normally be at the edges of the device so that they can be readily seen even when a patient is lying on the device. Such an arrangement may be provided in a movable cover or mat for a patient support, so that a patient may be positioned on the mat using the visible markings in any kind of radiotherapy apparatus—for example, the patient may be subject to a CT scan in a CT scanner, and subsequently subjected to treatment and/or imaging in an MRL; in this case, the patient can be positioned relative to the MR markers using the visible markings in a fairly consistent and reproducible manner in different radiotherapy systems. There are various computers involved in the system. In the TPS a treatment planning computer develops a treatment plan which defines the treatment and passes this to a treatment control computer. This instructs each of the MLC control computer, chassis rotation control computer, and radiation control computer as to the operation of their specific item during the treatment. The TPS also comprises a device/accessory computer, which identifies the device(s) present in the bore of the scanner from the MR images, determines its/their position and orientation, and passes this information, together with the characteristics of the device relating to its effect on the radiotherapeutic beam drawn from the database, to the treatment planning computer which adjusts the treatment plan accordingly. In practice, it will be necessary to decide whether each of these computers should exist as a separate entity or whether some or all should be combined into a single processor. This decision will depend on the pattern of expected computational load and the processing power available.

Such a treatment plan can be implemented on a radiotherapy machine that is substantially akin to those in current use. The physical differences called for by this invention lie in the devices/accessories used and the treatment planning apparatus (TPS); the actual radiotherapy apparatus and the means for driving it, its MLC and other systems, and the MR scanner can be as those in current use.

The invention encompasses the database, methods of populating it with device-specific data, and methods of using the apparatus. Where the term device is used, this should be construed as encompassing any accessory, couch, table, patient support, replaceable top surfaces therefor, frame, RF imaging coils, associated stand/s and any other item other than the patient which is used in any type of radiotherapeutic apparatus, and/or may in use be positioned within the field of an MRL during operation of the system.

BRIEF DESCRIPTION OF THE DRAWINGS

The invention will now be described by way of example and with reference to the accompanying figures, in which.

DETAILED DESCRIPTION OF THE EMBODIMENTS

Figure 1:
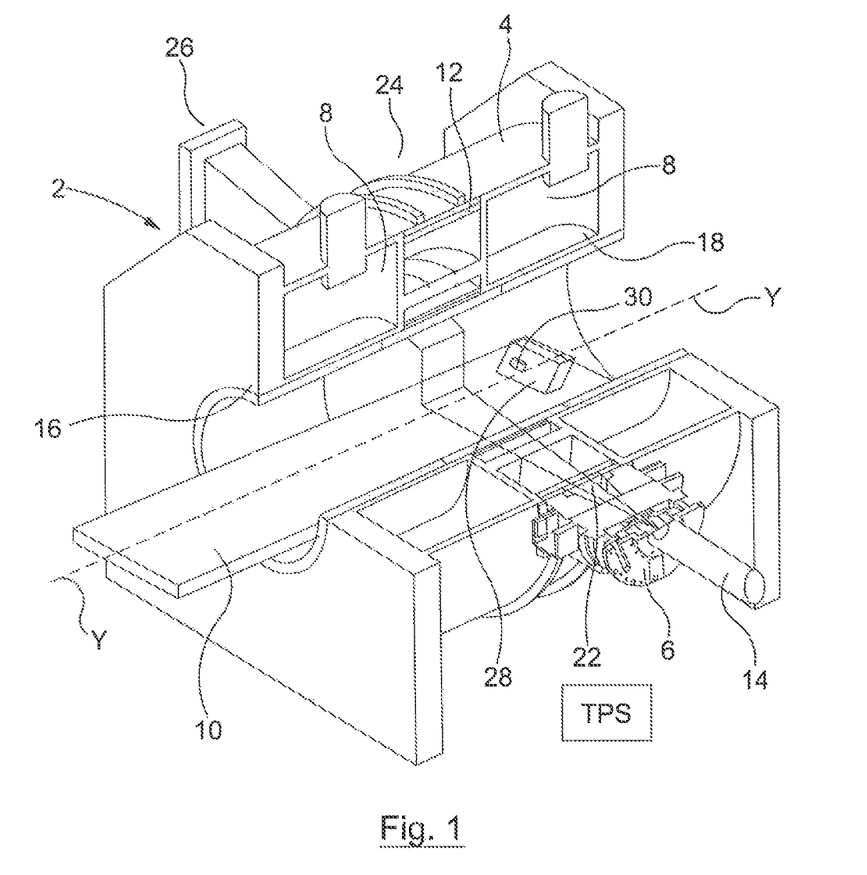
FIG. 1 shows a combined MRI and linear accelerator apparatus.

FIG. 1 shows a system 2 comprising a radiotherapy apparatus 6 and a magnetic resonance imaging (MRI) apparatus 4. The system includes a couch 10, for supporting a patient in the apparatus. The couch 10 is movable along a horizontal, translation axis (labelled "Y"), such that a patient resting on the couch is moved into the radiotherapy and MRI apparatus. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in our U.S. patent application Ser. No. 11/827,320 filed on 11 Jul. 2007.

As mentioned above, the system 2 also comprises an MRI apparatus 4, for producing near real-time imaging of a patient positioned on the couch 10. The MRI apparatus includes a primary magnet 8 which acts to generate the so-called "primary" magnetic field for magnetic resonance imaging. That is, the magnetic field lines generated by operation of the magnet 8 run substantially parallel to the central translation axis I. The primary magnet 8 consists of one or more coils with an axis that runs parallel to the translation axis Y; though not shown, the coils may be coaxial with the translation axis. The one or more coils may be a single coil or a plurality of coaxial coils of different diameter. As illustrated, the one or more coils in the primary magnet 8 are spaced such that a central window 12 of the magnet 8 is free of coils. In other embodiments, the coils in the magnet 8 may simply be thin enough that they are substantially transparent to radiation of the wavelength generated by the radiotherapy apparatus. The magnet 8 may further comprise one or more active shielding coils, which generates a magnetic field outside the magnet 8 of approximately equal magnitude and opposite polarity to the external primary magnetic field. The more sensitive parts of the system 2, such as the accelerator 14, are positioned in this region outside the magnet 8 where the magnetic field is cancelled, at least to a first order.

The MRI apparatus 4 further comprises two gradient coils 16, 18, which generate the so-called "gradient" magnetic field that is superposed on the primary magnetic field. These coils 16, 18 generate a gradient in the resultant magnetic field that allows spatial encoding of the protons so that their position can be determined, for example the gradient coils 16, 18 can be controlled such that the imaging data obtained has a particular orientation. The gradient coils 16, 18 are positioned around a common central axis with the primary magnet 16, and are displaced from one another along that central axis. This displacement creates a gap, or window, between the two coils 16, 18. In an embodiment where the primary magnet 8 also comprises a central window between coils, the two windows are aligned with one another.

An RF system causes the protons to after their alignment relative to the magnetic field. When the RF electromagnetic field is turned off the protons return to the original magnetization alignment. These alignment changes create a signal which can be detected by scanning. The RF system may include a single coil that both transmits the radio signals and receives the reflected signals, dedicated transmitting and receiving coils, or multi-element phased array coils, for example. Control circuitry controls the operation of the various coils 8, 16, 18 and the RF system, and signal-processing circuitry receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 14 (e.g. an x-ray source and a linear accelerator) and a multi-leaf collimator (MLC) 22, is mounted on a chassis 24. The chassis 24 is continuously rotatable around the couch 10 when it is inserted into the treatment area, powered by one or more chassis motors. In the illustrated embodiment, a radiation detector 26 is also mounted on the chassis 24 opposite the radiation source 14 and with the rotational axis of the chassis positioned between them. The radiotherapy apparatus 6 further comprises control circuitry, which (with the RF control circuitry) may be integrated within the system 2 shown in FIG. 1 or remote from it, and controls the radiation source 14, the MLC 22 and the chassis motor.

The radiation source 14 is positioned to deliver a beam of radiation through the window defined by the two gradient coils 16, 18, and also through the window 12 defined in the primary magnet 8. The radiation beam may be a cone beam or a fan beam, for example, and/or it may be shaped by the MLC to whatever shape is required by the treatment plan (within the design constraints of the particular MLC).

In operation, a patient is placed on the couch 10 and the couch is inserted into the treatment area defined by the magnetic coils 16, 18 and the chassis 24. The control circuitry controls the radiation source 14, the MLC 22 and the chassis motor to deliver radiation to the patient through the window 12 between the coils 16, 18. The chassis motor is controlled such that the chassis 24 rotates about the patient, meaning the radiation can be delivered from different directions. The MLC 22 has a plurality of elongate leaves oriented orthogonal to the beam axis; an example is illustrated and described in our EP-A-0,314,214, to which the reader is directed in order to obtain a full understanding of the described embodiment. The leaves of the MLC 22 are controlled to take different positions blocking or allowing through some or all of the radiation beam, thereby altering the shape of the beam as it will reach the patient. Simultaneously with rotation of the chassis 24 about the patient, the couch 10 may be moved along a translation axis into or out of the treatment area (i.e. parallel to the axis of rotation of the chassis). With this simultaneous motion a helical radiation delivery pattern is achieved, known to produce high quality dose distributions.

The MRI apparatus 4, and specifically the signal-processing circuitry, delivers real-time (or in practice near real-time) imaging data of the patient to the control circuitry. This information allows the control circuitry to adapt the operation of the MLC 22, for example, such that the radiation delivered to the patient accurately tracks the motion of the target region, for example due to breathing, so that the radiation received by the patient is in accordance with a predetermined treatment plan contained within the treatment planning system TPS. All the control circuitry and the TPS may be integrated in one or more computer processors, so as collectively to ensure that the patient is treated in accordance with the predetermined plan.

Figure 2:
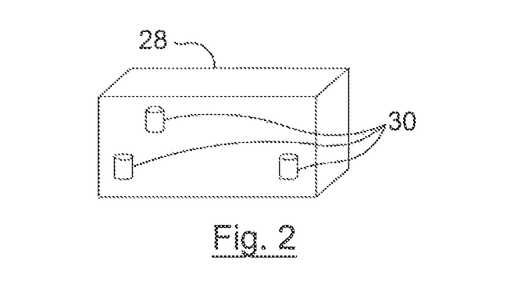
FIG. 2 is an enlarged schematic view of a device used within the field of the MR apparatus of FIG. 1.

Also shown in FIG. 1, and in greater detail in FIG. 2, (schematically, as a cuboid) is a device, or accessory, 28 such as a support for a part of the patient's body which is within the MR apparatus 4. The presence of this device 28 within the magnetic field of the MR apparatus 4 may be necessary to support the patient, to adjust the imaging field of the MR apparatus 4 or a combination of both. The device 28 will normally be solid, though it may be padded for patient comfort, flexible or adjustable, although it will usually retain its shape/configuration during operation of the system 2. The device may be part of, or placed on, the patient support (such as a cover therefor). The device will normally be substantially invisible to the MR scanner. However, device 28 will usually have some effect on the radiotherapeutic beam emitted by the radiotherapy apparatus 6 and, depending on the function of the device 28 (which will determine its size, shape, the materials of which it is made and where it is positioned in the system 2), it could have a significant effect on the radiotherapeutic beam. Unless the presence of the device 28 within the system 2 is taken into account, the actual radiotherapy received by the patient could differ from the radiation profile which is set out in the treatment plan. Moreover, even if the presence and location/orientation of the device 28 is input into the TPS, so as to allow for its effects on the radiotherapeutic beam, the device may move position and/or change its orientation during operation of the system 2; because the TPS has no way of identifying any such movement (because the device 28 is invisible to the MR scanner 4) the effect of the device 28 on the radiotherapeutic beam is unquantified, and the radiation dose applied to the patient will not be exactly according to the treatment plan.

As shown in FIG. 2, inside the device 28 are a number of MR markers 30; these markers are adapted to be visible in an MR scanner, such as those described in our co-pending British patent application, No. GB1305751.8. The illustration is of three such markers 30 within the device 28, though there could be one, two or more, and they could be located on the surface instead of/as well as within the device. The purpose of the markers 30 is to identify the device when viewed by the MR scanner, and to indicate the location and orientation of the device 28 within the system 2. This can be achieved by the number and relative locations of the markers, or a single marker could identify the device 28 and other markers indicate its location/orientation by their respective locations.

The geometry and the density profile of the device 28, and any other characteristics which might be significant in determining the effect of the device 28 on the radiotherapeutic beam, are stored in the TPS database (or a database accessible to the TPS) so that, when the MR scanner detects the device 28 and its position and orientation and communicates this information to the control circuitry and the TPS, the TPS can determine the effect the identified device 28 will have on the radiotherapeutic beam and adjust the radiotherapy apparatus appropriately (by controlling the beam intensity, beam shape (using the collimator 22), duration of irradiation and/or the beam angle (by rotating the radiotherapy apparatus around the chassis 24)) so as to ensure that the radiation dose received by the patient is precisely in accordance with the predetermined treatment plan. The database will have stored within it details of all the devices likely to be used within the system 2, so that recognition of the specific device and the adjustment to allow for its effect on the radiotherapeutic beam can be carried out automatically by the TPS; in addition, means can be provided to input into the database details of new devices as these become available for use with the system 2.

Figure 3A:
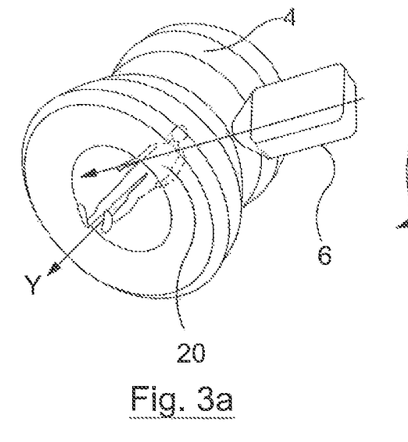
FIG. 3a is a schematic view of the MR radiotherapy apparatus of FIG. 1.
Figure 3B:
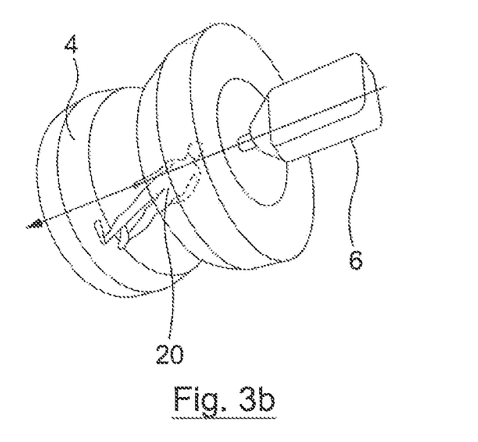
FIG. 3b is a schematic view similar to that of FIG. 3a but showing the MR apparatus and the radiotherapy apparatus arranged differently.

FIG. 3a shows schematically the arrangement of FIG. 1 with a patient 20 within the MR scanner 4 and the radiotherapy apparatus 6 adapted to rotate around the axis of the coils of the MR scanner 20; FIG. 3b shows an alternative arrangement, in which the patient 20 is positioned orthogonally to the axis of the MR scanner 20, and between the coils, and the radiotherapy apparatus 6 is aligned with the axis of the MR scanner. It is intended that the present invention be used in either of these configurations.

Figure 4:
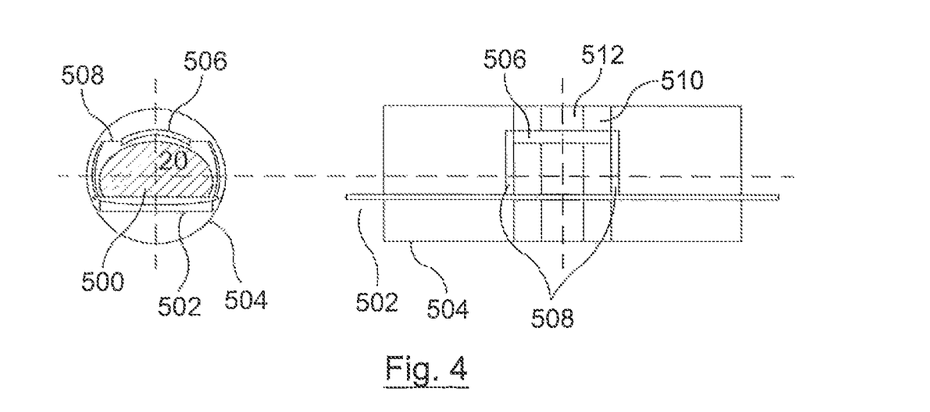
FIG. 4 shows, on the left, a cross sectional view in the axial plane of an MR-guided radiotherapy apparatus and, on the right, a side view in the sagittal plane of the apparatus.

Referring now to FIG. 4, this is an illustration of an arrangement similar to those of FIGS. 1 and 3a. Where like elements are shown in FIGS. 5a to 5e and referred to below, the same reference numeral as in FIG. 4 will be used, but with the suffix a to e as appropriate. FIG. 4 should be seen as a "key" to FIGS. 5a to 5e, reference numerals having been omitted from FIGS. 5a to 5e for greater clarity.

In FIG. 4, on the left is a view taken along the Y axis of FIG. 3a (i.e. an axial cross-section) and on the right is a view at right angles thereto (i.e. a sagittal cross-section view). A patient 20 is supported on a couch 502 within the bore 504 of an MR scanner, the bore defining the volume within which MR imaging takes place. To assist in imaging, RF coils need to be placed on either side of the patient; these imaging coils contain coils which are relatively resistant to radiation and associated electronics which are more sensitive to radiation. The coils are positioned so that they are in the region where the radiotherapy treatment is to be applied (so that an image of the region being treated can be generated during the treatment), but also so that the sensitive electronics are not in the path of the beam. The coil underneath the patient 20 can be placed in or under the couch 502, and thus its position is fixed. However, the coil 506 placed over the patient has to be put in position after the patient has been made to lie on the couch 502, therefore it has to be removable. The in the appropriate position RF coil 506 is placed on a stand 508 so it is supported over the body of the patient 20. The upper part of the stand 508 is adapted to engage with the coil 506, and the lower part of the stand 506 is adapted to engage with recesses or lugs on the couch 502, so that when assembled the coil 508 is accurately positioned so that, in use, the central, high intensity part of the radiotherapeutic beam 512 passes through the centre of the coil 508, and the sensitive electronics around the edge of the coil are in the outer, lower-intensity part of the beam 510 (or outside the beam entirely). The stand 508 and/or the coil 506 are provided with MR markers so that they are visible to the MR scanner, as described above.

Figure 5:
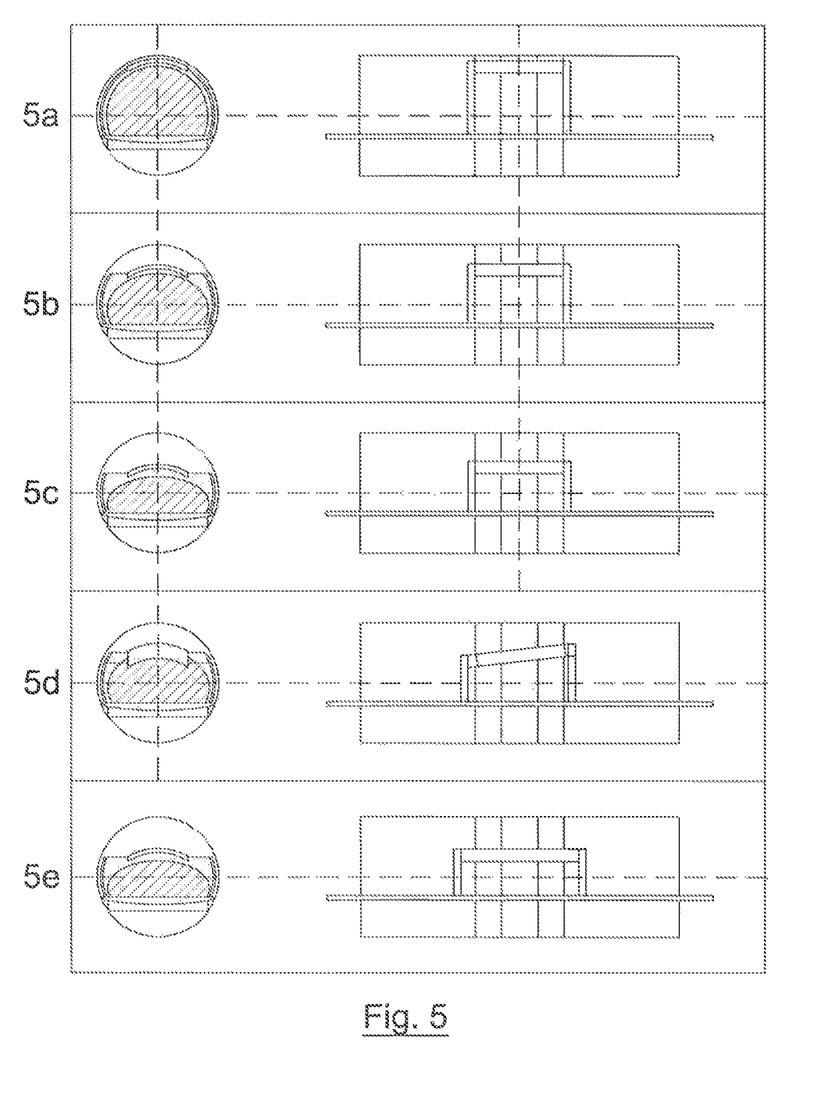
FIGS. 5a to 5e are views similar to those of FIG. 3 but including different devices/accessories within the apparatus.

FIG. 5 illustrates different arrangements of coil and frame. FIG. 5a shows a large anterior coil frame in which the frame 508a is adapted to follow the profile of the bore 504a (so as to maximise the size of patient who could be accommodated) and to support the coil 506a above a large patient. FIG. 5b shows a medium anterior coil frame 508b, for a medium sized patient, where the frame 508b is adapted to follow the profile of the bore 504b and is noticeably shorter than the frame 508a, and (coils 506a and 506b being the same) it has a horizontal portion extending over the sides of the patient. FIG. 5c is a small anterior coil frame 508c, for a small patient. FIG. 5d shows an angled anterior coil frame 508d, where (as seen clearly in the right hand picture) the frame has a stepped height to enable the rigid coil 506d to more closely follow the profile of a patient having a bulbous stomach. FIG. 5e shows an enhanced length anterior coil frame 508e, in which the coil 506e is larger than that in the preceding drawings so as to allow the couch 502e to be moved longitudinally if the tumour or region being treated has shifted during a treatment, which avoids the necessity of manually repositioning the frame 508e and coil 506e. Other frame and coil combinations will be used from time to time, and so this list is not exhaustive.

Each of the frames in FIGS. 5a to 5e is slightly different and is intended to be used in specific treatment plans. As described above, the system 2 can automatically detect, identify and adjust for the effects on the beam of a particular frame/coil combination. If the treatment plan included details of a particular combination which was intended to be used, but a different combination was used (by accident, such as where the frames appear similar—508b and 508c, for example) the TPS can detect the deviation from the predetermined plan and make the appropriate adjustments so that the patient receives the correct radiation dose. Alternatively or additionally the TPS can alert an operator that it has detected a device present within the MRL other than one which has been detailed in the predetermined treatment plan. However, this is wasteful of processor power; it may be quicker to replace the stand with the correct one, but even this is wasteful of time which should be used for treatment. Accordingly the coils 506 and stands 508 are provided with visible markings—symbols, words, colours, barcodes or combinations of these—so that it will be apparent to an operator which coil/frame is in use, so that this can be checked as correct against the predetermined treatment plan and so avoid wasting valuable system time and/or processor effort.

It will of course be understood that many variations may be made to the above-described embodiment without departing from the scope of the present invention. For example, the radiotherapy apparatus may comprise more than one source of therapeutic radiation and more than one respective multi-leaf collimator. There may only be one MR marker for a particular device/accessory, with that marker being adapted to fulfil both the identification function and to indicate position and orientation. Where there is an RF coil and a supporting frame, the sensitive electronics associated with the coil could be located in the frame so as to place them as far away as possible from the highest intensity of radiation (which is toward the centre of the beam 512), with the necessary electrical connections being made as the coil and frame are assembled for use. A projection system with an optical scanner may be used, and/or there could be colour-coded engagements (lugs, recesses, etc.), for ensuring the correct frame or other device is located correctly relative to the patient support. The marker(s) and/or MR marker(s) may be positioned adjacent to visible markings provided on the device, or they are in a known positional relationship thereto so that this information can be included in the TPS database. The device may be a mat or cover for a patient support, and this could be used in a system other than an MRL (e.g. a CT scanner), so that non-MRI images of a patient may be acquired with the MR markers being visible in such images, and these images may be directly comparable with those from an MR scanner because the patient is positioned on the same mat in each case, or the mat may be used only with the non-MR system but is constructed so that its MR marker(s) is/are positioned and/or oriented in a similar way as the MR marker(s) provided in or on the patient support in an MRL where the patient is subsequently to be scanned/treated. Where different variations or alternative arrangements are described above, it should be understood that embodiments of the invention may incorporate such variations and/or alternatives in any suitable combination.

The invention claimed is:

1. A radiotherapy system, comprising:
   a magnetic resonance (MR) scanner configured to produce images of an object within an imaging volume;
   a radiotherapy apparatus including a source of therapeutic radiation configured to deliver a beam of radiation into the object;
   a treatment planning system comprising a computer processor configured to control the source of therapeutic radiation to deliver the beam of radiation in accordance with a predetermined treatment plan and with the images of the object;
   a first marker device situated at least partially within the imaging volume, wherein the first marker device includes a plurality of imaging markers visible to the MR scanner; and
   a database configured to store data associated with a range of different marker devices, the range of different marker devices including the first marker device, wherein each marker device in the range of different marker devices includes a plurality of respective imaging markers, wherein the data associated with each marker device in the range of different marker devices includes:
      identification data identifying each marker device, wherein for each marker device in the range of different marker devices, the identification data identifies the number of imaging markers associated with the marker device and the spatial disposition of the imaging markers relative to the marker device, and
      geometric and density characteristic data of each marker device, wherein for each marker device in the range of different marker devices, the geometric characteristic data reflects a geometry of the marker device and the density characteristic data reflects a density of at least a portion of the marker device;
   wherein the computer processor of the treatment planning system is configured to:
      receive, from the MR scanner, data relating to the first marker device, the data relating to the first marker device including data relating to the number of imaging markers associated with the first marker device and the spatial disposition of the imaging markers relative to the first marker device,
      identify the first marker device from the range of different marker devices based on the data relating to the number of imaging markers associated with the first marker device and the spatial disposition of the imaging markers relative to the first marker device and based on the identification data identifying each marker device in the range of different marker devices,
      receive the geometric and density characteristic data of the identified first marker device from the database,
      determine a position or an orientation of the first marker device based on the identification data identifying the first marker device and the data relating to the first marker device received from the MR scanner, and
      adjust the predetermined treatment plan based on the determined position or orientation of the first marker device and based on the geometric and density characteristic data of the first marker device received from the database.

2. The radiotherapy system according to claim 1, wherein the determination of the position or the orientation of the first marker device is based at least in part on the data relating to the number of imaging markers associated with the first marker device and the spatial disposition of the imaging markers relative to the first marker device.

3. The radiotherapy system according to claim 1, wherein the first marker device includes visible identification or positional markings.

4. The radiotherapy system according to claim 3, wherein the visible identification or positional markings are situated outside of the imaging volume during a radiotherapy session.

5. The radiotherapy system according to claim 1, wherein the computer processor of the treatment planning system is configured to perform the adjustment of the predetermined treatment plan during a radiotherapy session.

6. The radiotherapy system according to claim 1, wherein at least one of the imaging markers associated with the first marker device is situated within an internal volume of the first marker device.

7. The radiotherapy system according to claim 1, wherein the computer processor of the treatment planning system is configured to:
   use the geometric and density characteristic data of the first marker device received from the database to determine an effect of the first marker device on the beam of radiation; and
   perform the adjustment of the predetermined treatment plan in order to negate the determined effect of the first marker device on the beam of radiation.

8. The radiotherapy system according to claim 1, wherein the source of therapeutic radiation is a linear accelerator.

9. A radiotherapy device that delivers a beam of radiation into an object, wherein the radiotherapy device is configured to communicate with a magnetic resonance (MR) scanner configured to produce images of the object within an imaging volume, the radiotherapy device comprising:

a source of therapeutic radiation configured to deliver the beam of radiation into the object in accordance with a predetermined treatment plan; and a processor configured to:

receive, from the MR scanner, data relating to a first marker device situated at least partially within the imaging volume, the first marker device including a plurality of imaging markers visible to the MR scanner, wherein the data relating to the first marker device includes data relating to the number of imaging markers associated with the first marker device and the spatial disposition of the imaging markers relative to the first marker device;

communicate with a database configured to store data associated with a range of different marker devices for use with the MR scanner, the range of different marker devices including the first marker device, wherein each marker device in the range of different marker devices includes a plurality of respective imaging markers, wherein the data associated with each marker device in the range of different marker devices includes:

geometric and density characteristic data of each marker device, wherein for each marker device in the range of different marker devices, the geometric characteristic data reflects a geometry of the marker device and the density characteristic data reflects a density of at least a portion of the marker device, and identification data identifying each marker device, wherein for each marker device in the range of different marker devices, the identification data identifies the number of imaging markers associated with the marker device and the spatial disposition of the imaging markers relative to the marker device;

identify the first marker device from the range of different marker devices based on the data relating to the number of imaging markers associated with the first marker device and the spatial disposition of the imaging markers relative to the first marker device and based on the identification data identifying each marker device in the range of different marker devices;

receive the geometric and density characteristic data of the identified first marker device from the database;

determine a position or an orientation of the first marker device based on the identification data identifying the first marker device and the data relating to the first marker device received from the MR scanner; and adjust the predetermined treatment plan based on the determined position or orientation of the first marker device and based on the geometric and density characteristic data of the first marker device received from the database.

10. The radiotherapy device according to claim 9, wherein the determination of the position or the orientation of the first marker device is based at least in part on the data relating to the number of imaging markers associated with the first marker device and the spatial disposition of the imaging markers relative to the first marker device.

11. The radiotherapy device according to claim 9, wherein the identification data identifying the first marker device includes:

data relating to a first imaging marker associated with the first marker device indicative of an identity of the first marker device, and data relating to a second imaging marker associated with the first marker device indicative of the position or the orientation of the first marker device.

12. The radiotherapy device according to claim 11, wherein the processor is configured to:

perform the identification of the first marker device from the range of different marker devices based on the data relating to the first imaging marker associated with the first marker device; and perform the determination of the position or the orientation of the first marker device based on the data relating to the second imaging marker associated with the first marker device.

13. The radiotherapy device according to claim 9, wherein the processor is configured to:

use the geometric and density characteristic data of the first marker device received from the database to determine an effect of the first marker device on the beam of radiation; and to perform the adjustment of the predetermined treatment plan to negate the determined effect of the first marker device on the beam of radiation.

14. A computer-implemented method for use with a radiotherapy device including a source of therapeutic radiation that delivers a beam of radiation into an object in accordance with a predetermined treatment plan, wherein the radiotherapy device communicates with a magnetic resonance (MR) scanner configured to produce images of the object within an imaging volume, the method comprising:

receiving, from the MR scanner, data relating to a first marker device situated at least partially within the imaging volume, the first marker device including a plurality of imaging markers visible to the MR scanner, wherein the data relating to the first marker device includes data relating to the number of imaging markers associated with the first marker device and the spatial disposition of the plurality of imaging markers relative to the first marker device;

communicating with a database configured to store data associated with a range of different marker devices for use with the MR scanner, the range of different marker devices including the first marker device, wherein each marker device in the range of different marker devices includes a plurality of respective imaging markers, wherein the data associated with each marker device in the range of different marker devices includes:

geometric and density characteristic data of each marker device, wherein for each marker device in the range of different marker devices, the geometric characteristic data reflects a geometry of the marker device and the density characteristic data reflects a density of at least a portion of the marker device, and identification data identifying each marker device, wherein for each marker device in the range of different marker devices, the identification data identifies the number of imaging markers associated with the marker device and the spatial disposition of the imaging markers relative to the marker device;

identifying the first marker device from the range of different marker devices based on the data relating to the number of imaging markers associated with the first marker device and the spatial disposition of the imaging markers relative to the first marker device and based on the identification data identifying each marker device in the range of different marker devices;

receiving the geometric and density characteristic data of the identified first marker device from the database;

determining a position or an orientation of the first marker device based on the identification data identifying the first marker device and the data relating to the first marker device received from the MR scanner; and adjusting the predetermined treatment plan based on the determined position or orientation of the first marker device and based on the geometric and density characteristic data of the first marker device received from the database.

15. The computer-implemented method of claim 14, wherein determining the position or the orientation of the first marker device is based at least in part on the data relating to the number of imaging markers associated with the first marker device and the spatial disposition of the imaging markers relative to the first marker device.

16. The computer-implemented method of claim 14, further comprising:

determining an effect of the first marker device on the beam of radiation in the imaging volume based on the geometric and density characteristic data of the first marker device received from the database; and wherein adjusting the predetermined treatment plan reduces or negates the determined effect of the first marker device on the beam of radiation.

* * * * *

UNITED STATES PATENT AND TRADEMARK OFFICE
CERTIFICATE OF CORRECTION

PATENT NO. : 10,668,302 B2
APPLICATION NO. : 14/522336
DATED : June 2, 2020
INVENTOR(S) : Christopher Charles Knox et al.

Page 1 of 1

It is certified that error appears in the above-identified patent and that said Letters Patent is hereby corrected as shown below:

On the Title Page

Column 2, item (57), Line 1 of ABSTRACT, "A system or use with" should read --A system for use with--.

Signed and Sealed this
Fourteenth Day of July, 2020

Andrei Iancu
*Director of the United States Patent and Trademark Office*